(12) United States Patent
Boeren et al.

(10) Patent No.: US 8,680,101 B2
(45) Date of Patent: Mar. 25, 2014

(54) CRYSTALLINE PIMOBENDAN, PROCESS FOR THE PREPARATION THEREOF, PHARMACEUTICAL COMPOSITION AND USE

(75) Inventors: Marinus Maria Martinus Boeren, Bladel (NL); Rudolf Johannes Paridaans, Bladel (NL); Sanita Petkune, Riga (LV); Viesturs Lusis, Riga (LV); Dzintra Muceniece, Riga (LV)

(73) Assignee: Eurovet Animal Health B.V., Bladel (NL)

( * ) Notice: Subject to any disclaimer, the term of this patent is extended or adjusted under 35 U.S.C. 154(b) by 22 days.

(21) Appl. No.: 12/970,503

(22) Filed: Dec. 16, 2010

(65) Prior Publication Data

US 2011/0152283 A1    Jun. 23, 2011

(30) Foreign Application Priority Data

Dec. 18, 2009    (NL) ..................................... 1037569

(51) Int. Cl.
*C07D 403/04* (2006.01)
*A61K 31/501* (2006.01)
*A61P 9/00* (2006.01)

(52) U.S. Cl.
USPC ..................................... 514/252.06; 544/238

(58) Field of Classification Search
USPC ..................................... 544/238; 514/252.06
See application file for complete search history.

(56) References Cited

U.S. PATENT DOCUMENTS

| | | | |
|---|---|---|---|
| 4,361,563 A | 11/1982 | Austel et al. | |
| 6,710,046 B1 | 3/2004 | Matsumori | |
| 7,650,848 B2 * | 1/2010 | Brennan et al. | 114/222 |
| 7,985,422 B2 * | 7/2011 | Vaya et al. | 424/469 |
| 8,026,285 B2 * | 9/2011 | Bezwada | 514/772.3 |
| 2005/0203097 A1 * | 9/2005 | Folger et al. | 514/252.06 |
| 2008/0207629 A1 | 8/2008 | Folger et al. | |
| 2010/0009934 A1 * | 1/2010 | Rickles et al. | 514/64 |
| 2010/0057039 A1 * | 3/2010 | Lovich et al. | 604/502 |
| 2011/0112061 A1 * | 5/2011 | Hu et al. | 514/210.2 |
| 2012/0065165 A1 * | 3/2012 | Aspland et al. | 514/64 |
| 2012/0065212 A1 * | 3/2012 | Hebeisen et al. | 514/252.05 |

FOREIGN PATENT DOCUMENTS

| | | |
|---|---|---|
| EP | 0 330 052 | 8/1989 |
| EP | 0 439 030 | 7/1991 |
| EP | 2 199 291 | 6/2010 |
| JP | 2006-219452 | 8/2006 |
| WO | 2005/084647 | 9/2005 |

OTHER PUBLICATIONS

Endoh, Circulation Journal (2008), 72(12), 1915-1925.*
Wang, et al., Arzneimittel Forschung (2008), 58(11), 569-573.*
Obach, et al., Drug Metabolism and Disposition (2008), 36(7), 1385-1405.*
Fusellier, et al., J. Vet. Pharmacol. & Therap., (2008), 31(2), 150-155.*
Abraham, et al., Magyar Allatorvosok Lapja (2008), 130(2).*
Markert, et al., J. Pharmacol. & Toxicol. Methods, (2007), 56(2), 203-211.*
Toyohira, et al., Naunyn-Schmiedeberg's Archives of Pharmacol., (2005), 371(2), 107-113.*
Kanno, et al., J. Vet. Med. Sci. (2007), 69(4), 373-377.*
Sheridan et al., J. Med. Chem. (2007), 50(14), 3173-3184.*
Woolley, et al., Int. J. Applied Research in Vet. Med. (2007), 5(1), 43-48.*
Aiba, et al., Biolog. & Pharmaceut. Bull. (2005), 28(1), 114-119.*
Endoh, et al. (II), Expert Opin. Pharmacotherapy (2006), 7(16), 2179-2202.*
Ijuin, et al., Iryo Yakugaku (2006), 32(6), 489-496.*
Brixius, et al., Cardiovascular Drugs & Therapy (2005), 19(6), 423-428.*
Maruyama, et al., Autonomic Neuroscience (2005), 122(1-2), 100-106.*
Wang, et al. (II), Bioorg. & Med. Chem. Ltrs. (2005), 15(18), 4076-4084.*
Xu et al., "New Synthesis of Cardiotonic Agent Pimobendan Monohydrate", Hecheng Huaxue, vol. 7 Issue 2, (1999, pp. 194-197.
Dutch Search Report No. 1037569.

* cited by examiner

*Primary Examiner* — James O Wilson
*Assistant Examiner* — Cecilia M Jaisle
(74) *Attorney, Agent, or Firm* — Barnes & Thornburg LLP

(57) ABSTRACT

The invention relates to a pharmaceutical composition containing pimobendan as an active ingredient. The invention also relates to a crystalline form of pimobendan, as well as to a combination of said crystalline form with at least one other therapeutically active ingredient. Moreover, the invention relates to uses of said crystalline form, as well as to a pharmaceutical composition containing it. Finally, the invention relates to a process for preparing a crystalline form of pimobendan.

10 Claims, 15 Drawing Sheets

CRYSTALLINE PIMOBENDAN, PROCESS FOR THE PREPARATION THEREOF, PHARMACEUTICAL COMPOSITION AND USE

Disclosed embodiments relate to pharmaceutical compositions containing pimobendan as an active ingredient. They also relate to new crystalline forms of pimobendan, processes for the preparation thereof, as well as to the use of the crystalline pimobendan and pharmaceutical compositions.

Pimobendan, the structural formula of which is:

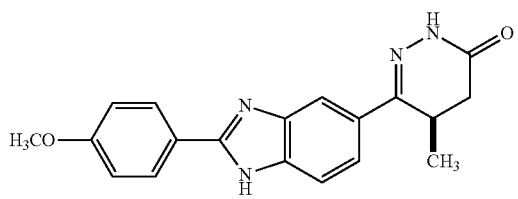 [SMILES: COc1ccc(-c2nc3cc(C4=NNC(=O)C[C@H]4C)ccc3[nH]2)cc1]

is a known active ingredient in medicinal products for cardiovascular therapy.

EP 0 439 030 discloses the low solubility of pimobendan in aqueous environments. The solubility is characterised by its highly pH-dependent nature. In humans, this lead to pimobendan blood contents which strongly fluctuate between individuals and are often too low. The unsatisfactory resorption behaviour is said to be caused by varying pH conditions in the gastrointestinal tract of individual subjects. According to EP 0 439 030, the low solubility and high pH-dependency of the solubility of pimobendan cannot be overcome by simultaneously administering an acid, but by intimately mixing pimobendan and citric acid in a ratio by weight of at least 1:5 or less. The palatability of orally administered forms is improved by a flavour-masking coating. The strongly fluctuating blood contents are said to be prevented by the acid microsphere, which itself is caused by the high dissolving rate of citric acid, formed around particles containing pimobendan. The microsphere is always acid and ensures a reliable, practically pH-independent dissolution and therefore resorption of pimobendan.

WO 2005/084647 discloses a solid formulation comprising pimobendan, which is homogeneously dispersed in (1) a polyvalent acid selected from the group consisting of acetic acid, tartaric acid or its anhydride, as well as (2) a flavoring substance. According to the publication, the high quantity of citric acid and the acidic taste thereof in the hard capsules disclosed in a EP 0 439 030 is not accepted by most subjects. This necessitates force-feeding or mixing with food prior to administration, which—according to WO 2005/084647—can be obviated by pimobendan being homogeneously disposed in both (1) one of the aforementioned polyvalent acids (or anhydride thereof) and (2) an acceptable flavouring substance.

SUMMARY

Disclosed embodiments provide a pharmaceutical composition containing crystalline pimobendan as an active ingredient, without an added not therapeutically active organic acid (or anhydride thereof).

Disclosed embodiments also provide new crystalline forms of pimobendan. The solubility characteristics of the crystalline forms are such that adding an organic acid or an anhydride thereof and a flavoring substance are not needed for ensuring a satisfactory dissolution rate and therefore satisfactory resorption of pimobendan. Moreover, the acceptance by the subjects is such that adding a flavoring substance is, in principle, not needed. In any case, force-feeding of subjects can be avoided with the present crystalline forms of pimobendan and present pharmaceutical compositions. Disclosed embodiments lead to a high compliance of the subjects to be treated.

Disclosed embodiments also relate to a pharmaceutical composition containing crystalline pimobendan as an active ingredient, without an added therapeutically active organic acid.

Disclosed embodiments also relate to a crystalline form of pimobendan selected from the group consisting of:
(i) form A, the diffraction pattern using powder X-ray diffractometry of which has peaks at Bragg angles (2θ) of 12.69°, 18.67° and 19.42° (with relative intensities of 9%, 100% and 37%, respectively) as the most characteristic peaks;
(ii) form B, the diffraction pattern using powder X-ray diffractometry of which has peaks at Bragg angles (2θ) of 4.65°, 12.90° and 20.70° (with relative intensities of 100%, 53% and 99%, respectively) as the most characteristic peaks;
(iii) form C, a dioxane solvate, of which the diffraction pattern using powder X-ray diffractometry of which has peaks at Bragg angles (2θ) of 7.88°, 14.45° and 17.94° (with relative intensities of 100%, 58% and 49%, respectively) as the characteristic peaks;
(iv) form D, a methanol solvate, of which the diffraction pattern using powder X-ray diffractometry of which has peaks at Bragg angles (2θ) of 11.20°, 12.82° and 20.80° (with relative intensities of 70%, 94% and 100%, respectively) as the most characteristic peaks.

Form A may also have the following characteristic peak using differential scanning calorimetry: one endothermic peak corresponding to melting at 241-244° C. Form A may also have the following characteristic peaks of the IR spectrum obtained by using infrared (IR) spectrometry, expressed in cm-1: 3200 (broad), 2900 (νC—H alif.; more intense than for form B); 1671 (νC═O), 837 (δC—H arom.), 810 (δC—H arom.).

Form B may also have the following characteristic peaks using differential scanning calorimetry: one first, broad, endothermic peak at 181-193° C. with a minimum at 188° C., an exothermic peak at 200-223° C. with a maximum at 212° C., and a second endothermic peak at 226° C. Form B may also have the following characteristic peaks of the IR spectrum obtained by using infrared (IR) spectrometry, expressed in cm-1: 3400 (small peaks), 2900 (νC—H alif.; smaller than with form A); 1793 (νC:O).

Form C may also have the following characteristic peaks using differential scanning calorimetry: desolvatation and melting at 147-153° C. with a minimum at 150° C., followed by recrystallisation at 185-217° C. with a maximum at 200° C., and two endothermic peaks at 223° C. and 237° C. Form C may also have the following characteristic peaks of the IR spectrum obtained by using infrared (IR) spectrometry, expressed in cm-1: 3055, 2840 (more intense than with form D), 1628, 872, 845, 808.

Form D may also have the following characteristic peaks using differential scanning calorimetry: desolvatation at 97-129° C. with a minimum at 117° C., melting at 137-162° C. with a minimum at 152° C., followed by recrystallisation and two endothermic peaks at 226° C. and 238° C. Form D may also have the following characteristic peaks of the IR spectrum obtained by using infrared (IR) spectrometry, expressed in cm-1: 3554, 2840 (very weak), 839, 823.

Disclosed embodiments also relate to the present crystalline form of pimobendan for use in therapy as a medicine. They also relate to the present crystalline form for use in the treatment of diseases, troubles or conditions in the cardiovascular field, of the renal system or of the respiratory system. Particularly, the diseases, troubles or conditions are: valvular insufficiency (e.g., mitral and/or tricuspid regurgitation) or dilated cardiomyopathy and hypertension.

Furthermore, disclosed embodiments also relate to a combination of the present crystalline form of pimobendan, to be used in therapy, and at least one other therapeutically active ingredient. The active ingredient may be selected from the group consisting of: a calcium channel blocker, aldosteron antagonist, loop diuretic, thiazide diuretic, prostaglandin, ACE inhibitor, digitalis glycoside, β-blocker, angiotensin II receptor antagonist, and phosphodiesterase type 5 inhibitor.

Moreover, disclosed embodiments also relate to a use of the present crystalline form of pimobendan for the manufacture of a medicine for treatment of diseases, troubles or conditions in the cardiovascular field, of the renal system or of the respiratory system. According to disclosed embodiments, the medicine can also contain at least one other therapeutically active ingredient. The other therapeutically active ingredient may be selected from the group consisting of: a calcium channel blocker, aldosteron antagonist, loop diuretic, thiazide diuretic, prostaglandin, ACE inhibitor, digitalis glycoside, n-blocker, angiotensin II receptor antagonist, and phosphodiesterase type 5 inhibitor.

Moreover, disclosed embodiments also relate to a method for treatment of diseases, troubles or conditions in the cardiovascular field, of the renal system or of the respiratory system which comprises administering to a patient in need of such treatment an effective amount of the crystalline form of pimobendan according to the disclosed embodiments. According to disclosed embodiments, further at least one other therapeutically active ingredient can be administered. The other therapeutically active ingredient may be selected from the group consisting of: a calcium channel blocker, aldosteron antagonist, loop diuretic, thiazide diuretic, prostaglandin, ACE inhibitor, digitalis glycoside, β-blocker, angiotensin II receptor antagonist, and phosphodiesterase type 5 inhibitor.

Disclosed embodiments also relate to a pharmaceutical composition, which contains a crystalline form of pimobendan according to disclosed embodiments as a therapeutically active ingredient, together with carriers and excipients. Disclosed embodiments also relate to the pharmaceutical composition, containing at least one other therapeutically active ingredient. The other therapeutically active ingredient is selected from the group consisting of: a calcium channel blocker, aldosteron antagonist, loop diuretic, thiazide diuretic, prostaglandin, ACE inhibitor, digitalis glycoside, β-blocker, angiotensin II receptor antagonist, and phosphodiesterase type 5 inhibitor. The pharmaceutical composition of the disclosed embodiments may be formulated in a form suited from oral administration.

The present crystalline form of pimobendan, combination of pharmaceutical composition containing it, is to be administered to a subject in need of a treatment therewith.

In particular, the subject is a patient, human or mammal, such as a dog, suffering from diseases, troubles or conditions in the cardiovascular field, of the renal system or of the respiratory system.

The amount of the crystalline pimobendan of disclosed embodiments, also referred to herein as the active ingredient, which is required to achieve a therapeutic effect, that is the therapeutically effective amount, will vary with the crystalline form, the route of administration and the age and other conditions of the subject.

For a dog, suitable daily dosages are between 0.2 mg/kg and 0.6 mg/kg body weight of the subject.

The desired dose may be presented as one, two, three or more sub-doses administered at appropriate intervals throughout the day.

While it is possible for the active ingredient to be administered as such, it is preferable to present it as a pharmaceutical formulation. Accordingly, disclosed embodiments provide a pharmaceutical formulation comprising pure crystalline pimobendan, together with a pharmaceutically acceptable carrier therefor and optionally other therapeutic agents. The carrier must be "acceptable" in the sense of being compatible with the other ingredients of the formulation and not deleterious to the recipients thereof. Suitable excipients are described in standard manuals, e.g., in the Handbook of Pharmaceutical Excipients, 3th Edition; A. H. Kibbe. American Pharmaceutical Association and Pharmaceutical Press, 2000. Disclosed embodiments further include a pharmaceutical formulation, as hereinbefore described, in combination with packaging material suitable for the pharmaceutical formulation, the packaging material including instructions for therapeutically using of the pharmaceutical formulation.

Formulations are in particular those suitable for oral administration. The formulations may be prepared by any methods well known in the art of pharmacy, for example, using methods such as those described in Gennaro et al., Remmington: The Science and Practice of Pharmacy, 20th Edition, Lippincott, Williams and Wilkins, 2000; see especially part 5: pharmaceutical manufacturing. Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as tablets or capsules, each containing a predetermined amount of active ingredient; as a powder or as granulates; as a solution, an emulsion or a suspension. The active ingredient may also be presented as a paste, or may be contained within liposomes or microparticles. The formulation may also be administered as a bolus.

In the context of the disclosed embodiments, the use of crystalline pimobendan in a therapeutical context does not exclude the use of any other active ingredient for treatment of the condition to be treated. The other active ingredient can be administered before, simultaneously with, or after crystalline pimobendan according to disclosed embodiments. Crystalline pimobendan can even be combined together with the other active compound into one pharmaceutical composition. The expert will recognize that, in each case of combined use or add—on therapy, the doses and/or formulations may have to be adapted accordingly.

Finally, disclosed embodiments relate to a process for the preparation of crystalline form A of pimobendan, a process for the preparation of crystalline form B of pimobendan, a process for the preparation of crystalline form C of pimobendan, and a process for the preparation of crystalline form D of pimobendan. The crystalline forms of disclosed embodiments are prepared starting from pimobendan monohydrate, the preparation of which is described in Example 1.

Disclosed embodiments relate to a process for the preparation of crystalline form C of pimobendan, wherein
(i) pimobendan monohydrate is dissolved in 1,4-dioxane, whereupon the solution is boiled, and the filtrate obtained following hot filtration is cooled to 15-20° C., whereby a precipitate is formed;
(ii) the precipitate formed in (i) is filtered and dried under low pressure and at 60-70° C., whereby crystalline form C of pimobendan according to disclosed embodiments is obtained as a white powder.

Disclosed embodiments also relate to a process for the preparation of crystalline form A of pimobendan, wherein
(i) pimobendan monohydrate is dissolved in 1,4-dioxane, whereupon the solution is boiled, and the filtrate obtained following hot filtration is cooled to 15-20° C., whereby a precipitate is formed;
(ii) the precipitate formed in (i) is filtered and dried under low pressure and at 60-70° C., whereby the crystalline dioxane solvate of pimobendan according to disclosed embodiments is obtained as a white powder;
(iii) the dioxane solvate of pimobendan obtained in (ii) is stirred in toluene, is heated to the boiling temperature and is subjected to hot filtration; whereupon
(iv) the precipitate obtained in (iii) is washed with toluene and is dried under low pressure and at 115-120° C., whereupon the crystalline form A of pimobendan according to disclosed embodiments is obtained as a white powder.

Moreover, disclosed embodiments relates to a process for the preparation of crystalline form D of pimobendan, wherein
(i) pimobendan monohydrate is dissolved in 1,4-dioxane, whereupon the solution is boiled, and the filtrate obtained following hot filtration is cooled to 15-20° C., whereby a precipitate is formed;
(ii) the precipitate formed in (i) is filtered and dried under low pressure and at 60-70° C., whereby crystalline form C of pimobendan according to disclosed embodiments is obtained as a white powder;
(iii) the dioxane solvate of pimobendan obtained in (ii) is stirred in toluene, is heated to the boiling temperature and is subjected to hot filtration; whereupon
(iv) the precipitate obtained in (iii) is washed with toluene and is dried under low pressure and at 115-120° C., whereupon the crystalline form A of pimobendan according to disclosed embodiments is obtained as a white powder; whereupon
(v) crystalline form A of pimobendan obtained in (iv) is ground with methanol under a dry atmosphere until the metanol is evaporated, whereby crystalline form D of pimobendan according to disclosed embodiments is obtained as a white powder.

Furthermore, disclosed embodiments relates to a process for the preparation of crystalline form B of pimobendan, wherein
(i) pimobendan monohydrate is dissolved in 1,4-dioxane, whereupon the solution is boiled, and the filtrate obtained following hot filtration is cooled to 15-20° C., whereby a precipitate is formed;
(ii) the precipitate formed in (i) is filtered and dried under low pressure and at 60-70° C., whereby crystalline form C of pimobendan according to disclosed embodiments is obtained as a white powder;
(iii) the dioxane solvate of pimobendan obtained in (ii) is stirred in toluene, is heated to the boiling temperature and is subjected to hot filtration, whereupon
(iv) the precipitate obtained in (iii) is washed with toluene and is dried under low pressure and at 115-120° C., whereupon the crystalline form A of pimobendan according to disclosed embodiments is obtained as a white powder; whereupon
(v) crystalline form A of pimobendan obtained in (iv) is ground with methanol under a dry atmosphere until the metanol is evaporated, whereby the crystalline methanol solvate of pimobendan according to disclosed embodiments is obtained as a white powder, whereupon
(vi) the crystalline methanol solvate of pimobendan obtained in (v) is heated at 60-70° C., whereby crystalline form B of pimobendan according to disclosed embodiments is obtained as a white powder.

The methods used for analyzing crystalline forms of pimobendan are described hereinafter.

Materials and methods used for analysing crystalline forms of pimobendan.

Powder X-Ray Diffraction Analysis.

PXRD patterns were determined on a Bruker D8 Advance diffractometer using copper radiation (CuKα) at a wavelength of 1.54180 Å. The tube voltage and current were set to 40 kV and 40 mA. The divergence and scattering slits were set at 1.0 mm, and the receiving slit was set at 0.6 mm. The diffraction patterns were taken using a scanning speed 0.5 s/0.02o from 3o to 30o in 2☐scale. Samples were packed into glass holders with weight capacity of 50-200 mg.

Thermal Methods of Analysis.

A METTLER TOLEDO DSC 823e instrument was used for the measurement of melting point and transition temperature of each form. The measurements were made using aluminium sample pans; the sample weight was (5-15) mg at a heating rate of 10° C./min in interval from 40° C. to 270° C. Transition temperatures and melting points were determined as the point of intersection between the base line and the linear section of the ascending endothermic curve.

The melting temperature of crystalline form A of pimobendan was 241-244° C., the melting temperature of crystalline form B of pimobendan was 188° C., the melting temperature of crystalline form C of pimobendan was 127-160° C.

Fourier Transform Infrared Spectroscopy.

Powdered sample FTIR patterns were made with ATI FTIR FM, ATI MATTISON spectrophotometer in KBr pellets. Approximately 1 mg of sample was ground with 400 mg of KBr and a 100 mg tablet of this mixture was made using a GRASEBY SPECAL press. KBr from Across Organics was used for IR spectroscopy.

Gas Chromatography (GC).

To determine the residual solvent content in pimobendan solvate, a GC headspace method was used. Analyses were carried out on an Agilent Technologies 6850 instrument using flame ionization detector (250° C.) with a helium flow rate of 3.0 ml/min. A DB-624 (30 m×0.53 mm, film thickness 3 mm) column was used, the injection temperature was 200° C. The temperature regime of analysis was as follows: oven at 40° C. for 10 min, then at a rate 10 o per minute to 240° C., split ratio 3:1.

High Performance Liquid Chromatography (HPLC).

Related substances content of pimobendan crystalline forms was determined by an HPLC method. Analyses were performed on a Waters 2695 Alliance liquid chromatograph, with a detection wavelength of 290 nm. A Waters Symmetry C18 3.9×150 mm (5 ☐m particle diameter) column was used, and the column temperature was set to 45° C. The mobile phase was a 0.022 M potassium dihydrogen phosphate (KH2PO4) buffer solution (pH 2.5) (A) and acetonitrile (B). The flow rate of the mobile phase was 1.0 ml/min, and the injection volume was 10 ☐l. Test solutions were prepared at concentrations of 5.0 mg/ml. For equilibration one gradient cycle was used (according to the Ph. Eur. Pimobendan monograph).

| Gradient table: | | |
|---|---|---|
| Time, min | Mobile phase A (V/V), % | Mobile phase B (V/V), % |
| 0-6 | 85→80 | 15→20 |
| 6-20 | 80→20 | 20→80 |
| 20-20.1 | 20→85 | 80→15 |
| 20.1-30 | 85 | 15 |

1H-NMR Spectroscopy.

1H-NMR spectra were recorded on a Varian 400 Mercury spectrometer at 400 mHz on sample solutions in borosilicate glass 175×5 mm sample tubes (Wilmad; Buena, N.J.) using DMSO-d6 as solvent. Samples were prepared with a concentration of 5 mg/ml. The proton signal for hexamethyldisiloxane (0.055 ppm) was used as an internal reference for 1H-NMR spectra. Coupling constants were reported in Hz.

Element Analysis.

Element analysis (C, H, N, and O) was carried out on a Carlo Erba EA-1180 elemental analyzer. The conditions of analysis were as follows: sample—net; sample size—1.5 mg; combustion gas—oxygen; combustion temperature—1000° C.

Loss on Drying.

An accurately weighted sample of approximately 1.0 g was dried in an oven at (105□2) ° C. temperature for 4 hours (method Ph. Eur., 2.2.32.).

Carl Fisher titration—KFT water determination.

A Metrohm 799 GPT Titrino Karl Fischer volumetric titration was used for semi-micro determination of water in samples. Approximately 500 mg of a sample was accurately weighted and titrated with KF reagent Hydranal—Composite 5. The KF reagent titer was approximately 5 mg/ml.

DETAILED DESCRIPTION

Example 1

Synthesis of Pimobendan Monohydrate

The starting material, 4-chlorophenylaldehyde, was reacted with crotononitrile in the presence of sodium cyanide, N,N-dimethylformamide and methanol. To the reaction product [(4-(4-chlorophenyl)-3-methyl-4-oxobutyronitrile], water and hydrochloric acid were added to obtain the acid [(4-(4-chlorophenyl)-3-methyl-4-oxobutyric acid]. Under the influence of nitric acid in water, the corresponding 3 nitro compound was formed [(4-(4-chloro-3-nitrophenyl)-3-methyl-4-oxobutyric acid].

With hydrazine hydrate and acetic acid in purified water, the 3 nitro compound was transferred to the double ring structure 6-(4-chloro-3-nitrophenyl)-5-methyl-4,5-dihydro-2H-pyradazin-3-one. This molecule was benzylated with benzylamine in a n-butanol/water mixture to form 6-(4-benzylamino-3-nitrophenyl)-5-methyl-4,5-dihydro-2H-pyridazin-3-one.

6-(4-Benzylamino-3-nitrophenyl)-5-methyl-4,5-dihydro-2H-pyridazin-3-one was mixed with methanol and a separately prepared mixture of Pd/C catalyst, water and hydrochloric acid. After hydrogenation, the reaction mixture was filtered and the filtrate was alkalined with a sodium hydroxide solution. The precipitate was filtered, rinsed with water and methanol, filtered and dried, to obtain 6-(3,4-diaminophenyl)-5-methyl-4,5-dihydro-2H-pyridazin-3-one.

This product was suspended in N,N'-dimethylformamide and sodium hydrosulphite was added. The mixture was heated to approximately 90° C. and p-anisaldehyde was added at 100 (95-105)° C. and the reaction was stirred at 100 (95-105)° C. After the reaction, the mixture was cooled with stirring to 20 (18-23)° C. and pimobendan monohydrate was precipitated by pouring into water. The precipitate was filtered, rinsed with purified water and the filter cake was rinsed with water and then suspended in boiling acetone, filtered while hot and the solids were dried at reduced pressure at 45 (40-50)° C., to obtain purified pimobendan monohydrate.

Figure 1A:
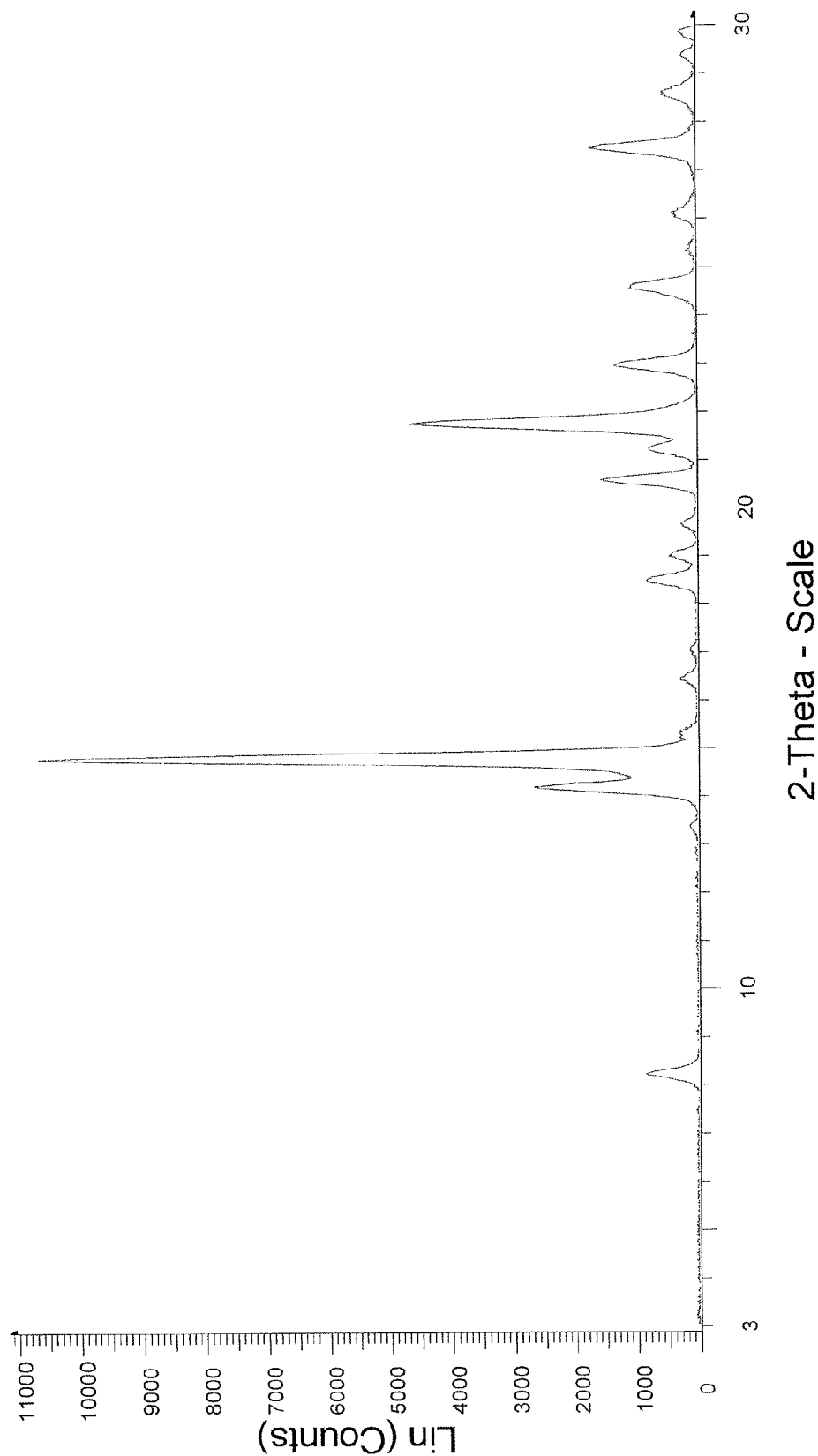
FIG. 1 represents the results of powder X-ray diffraction analysis (FIG. 1A), differential scanning calorimetry (DSC) (FIG. 1B) and infrared (IR) spectroscopy (FIG. 1C) of pimobendan monohydrate. The methods for detection and analysis were as described in the section "Materials and methods used for analysing crystalline forms of pimobendan".
Figure 1B:
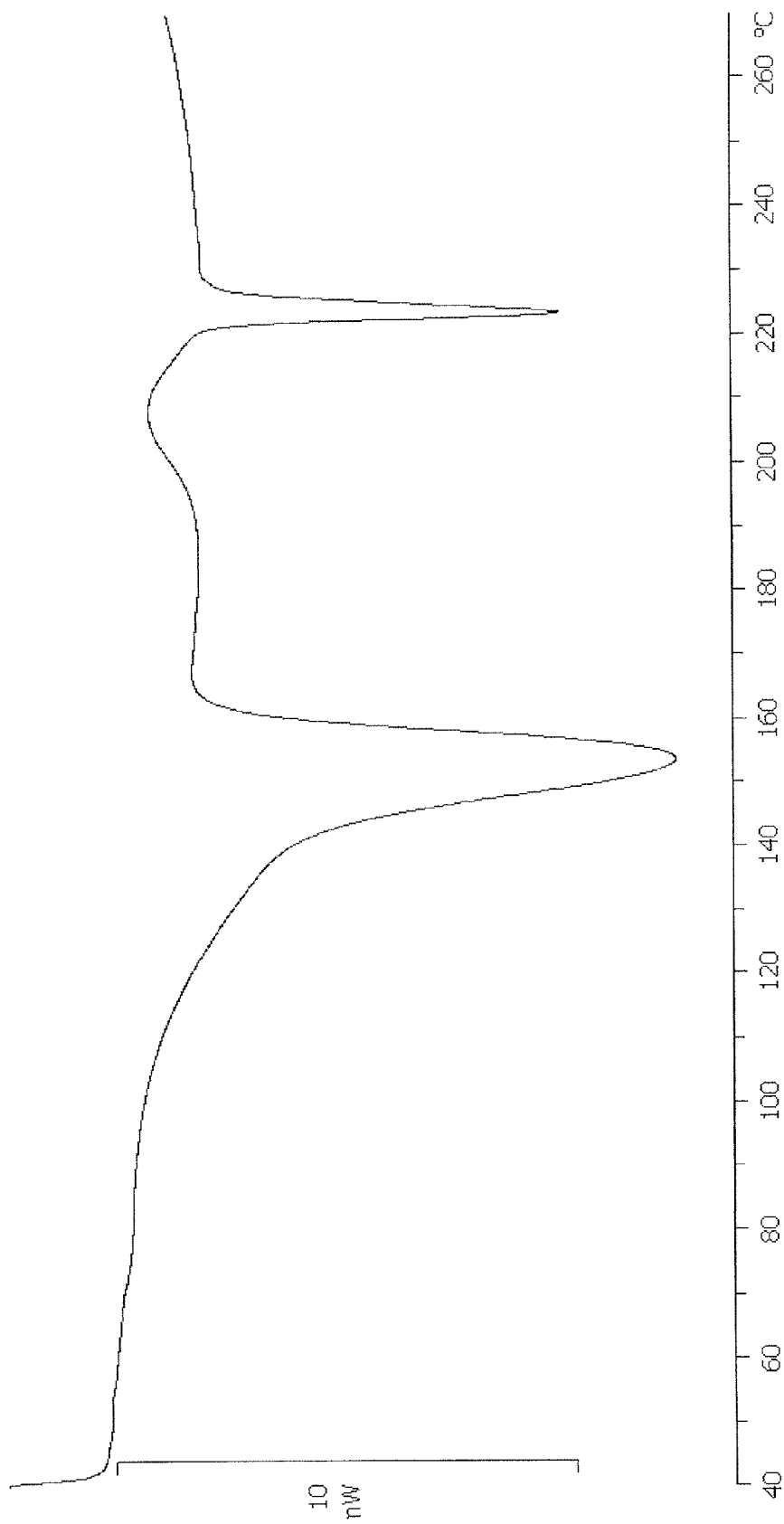
Figure 1C:
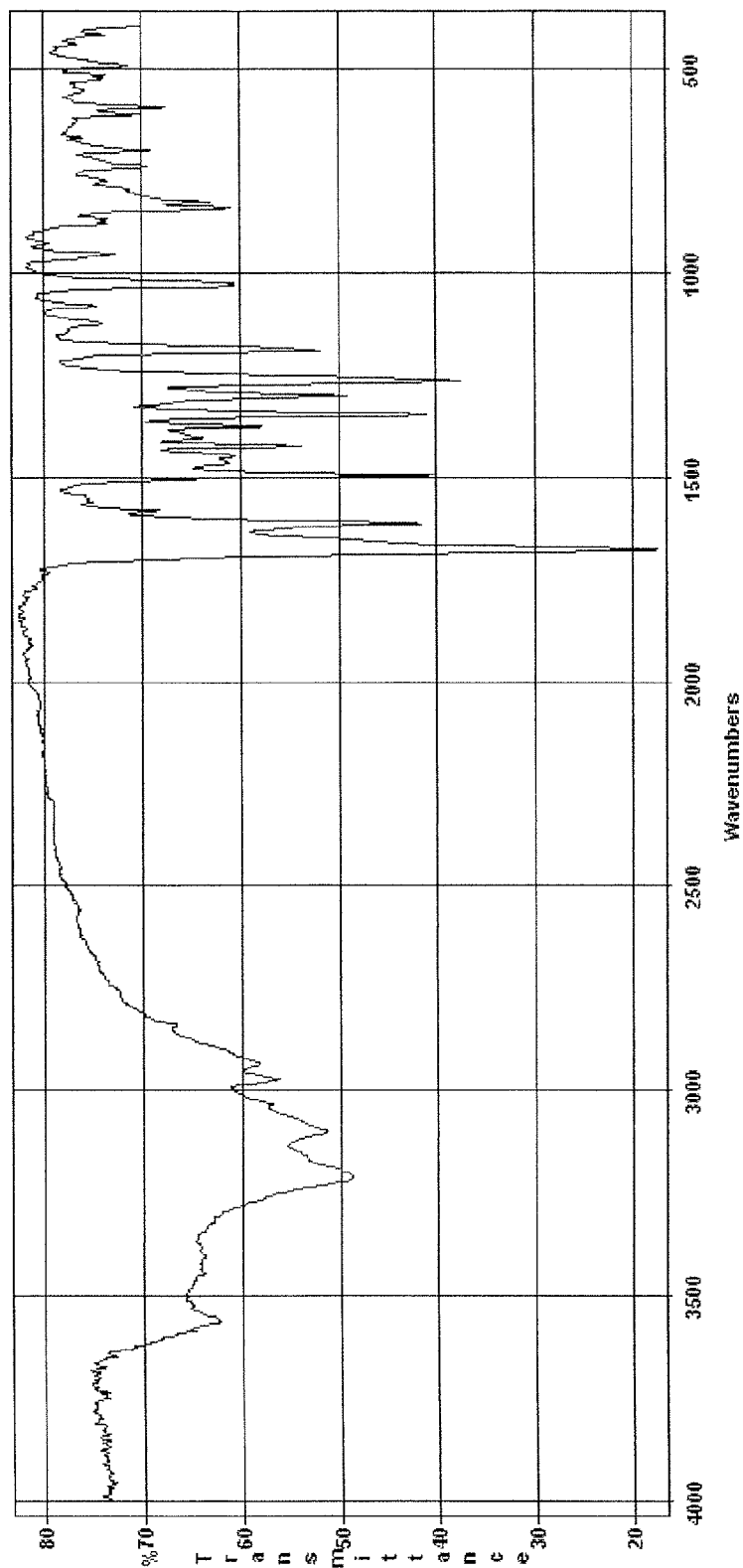

The results of the detection and analysis were represented in FIG. 1.

Example 2

Preparation of Pimobendan Crystalline Form C (Pimobendan Dioxane Solvate)

Pimobendan monohydrate (211.8 g, assay 92.8% relative to pimobendan nonsolvate, 0.5878 mol) was dissolved in 1,4-dioxane (2750±50 ml). The reaction mixture was heated to boiling temperature (99-100° C.), maintained at that temperature for 22 (15-30) minutes and the hot mixture was filtered on a suction funnel. The reaction mixture was cooled to 18 (15-20)° C. in approximately 2 hours, maintained at that temperature for 1.5 (2-3) hours and filtered on a suction funnel.

The precipitate was rinsed with 1,4-dioxane (250±20 ml). After that, the precipitate was filtered and dried at reduced pressure at 65 (60-70)° C. for about (6-8) hours, until loss on drying was less than 1.0%.

Pimobendan crystalline form C (pimobendan dioxane solvate) was obtained as white powder (227.1 g, assay 79.3%, related substances<0.05%, content of water 0.08%). The yield of this process was 91.6% (on average (91.3±1.5) %). The melting temperature was 127-160° C.

Figure 4A:
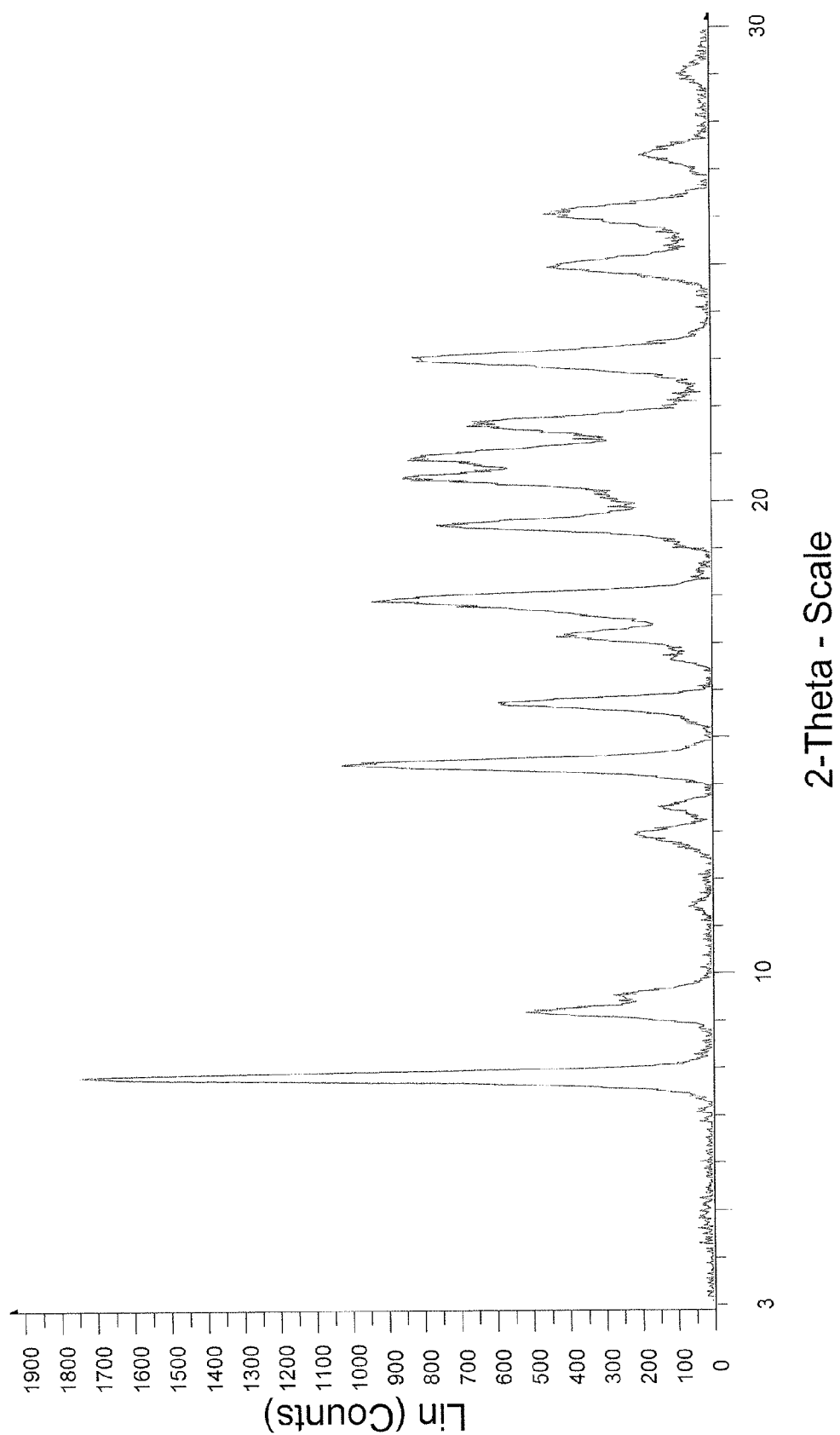
FIG. 4 represents the results of powder X-ray diffraction analysis (FIG. 4A), differential scanning calorimetry (DSC) (FIG. 4B) and infrared (IR) spectroscopy (FIG. 4C) of crystalline form C of pimobendan. The methods for detection and analysis were as described in the section "Materials and methods used for analyzing crystalline forms of pimobendan".
Figure 4B:
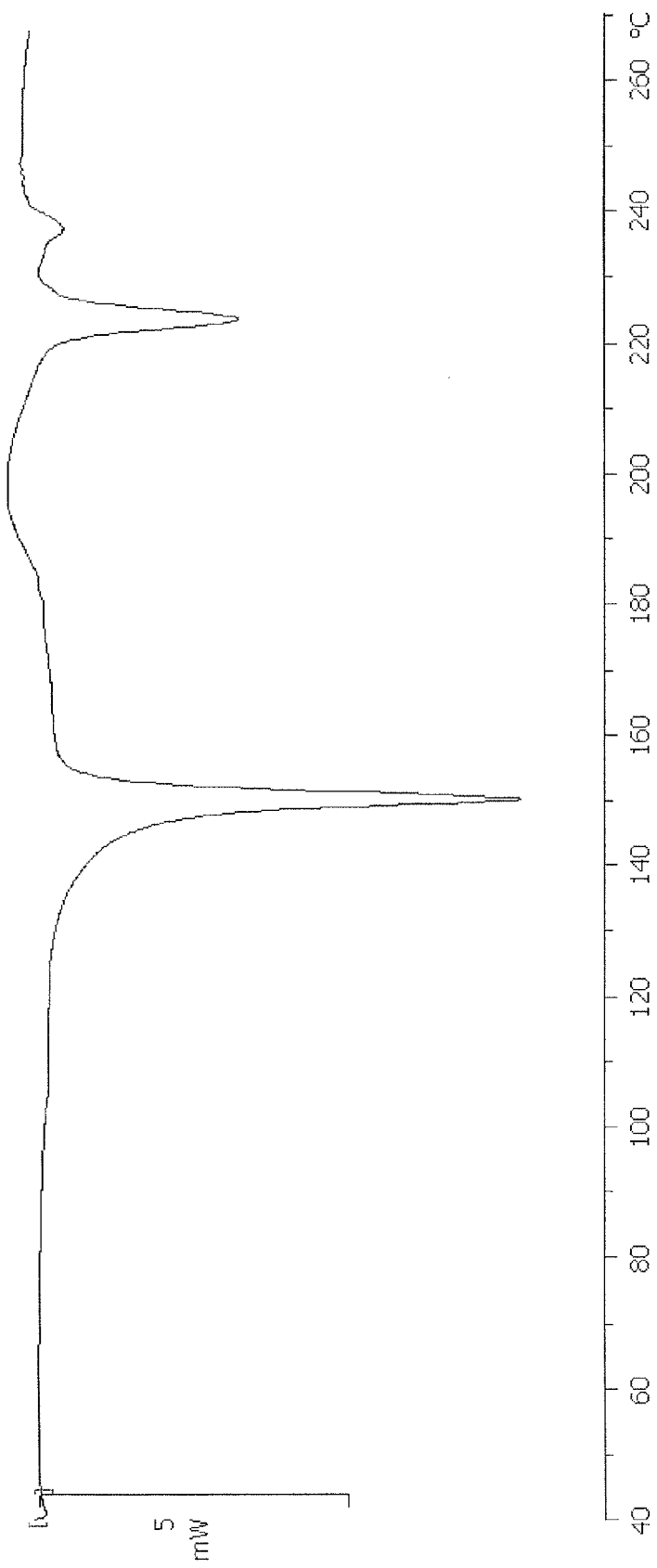
Figure 4C:
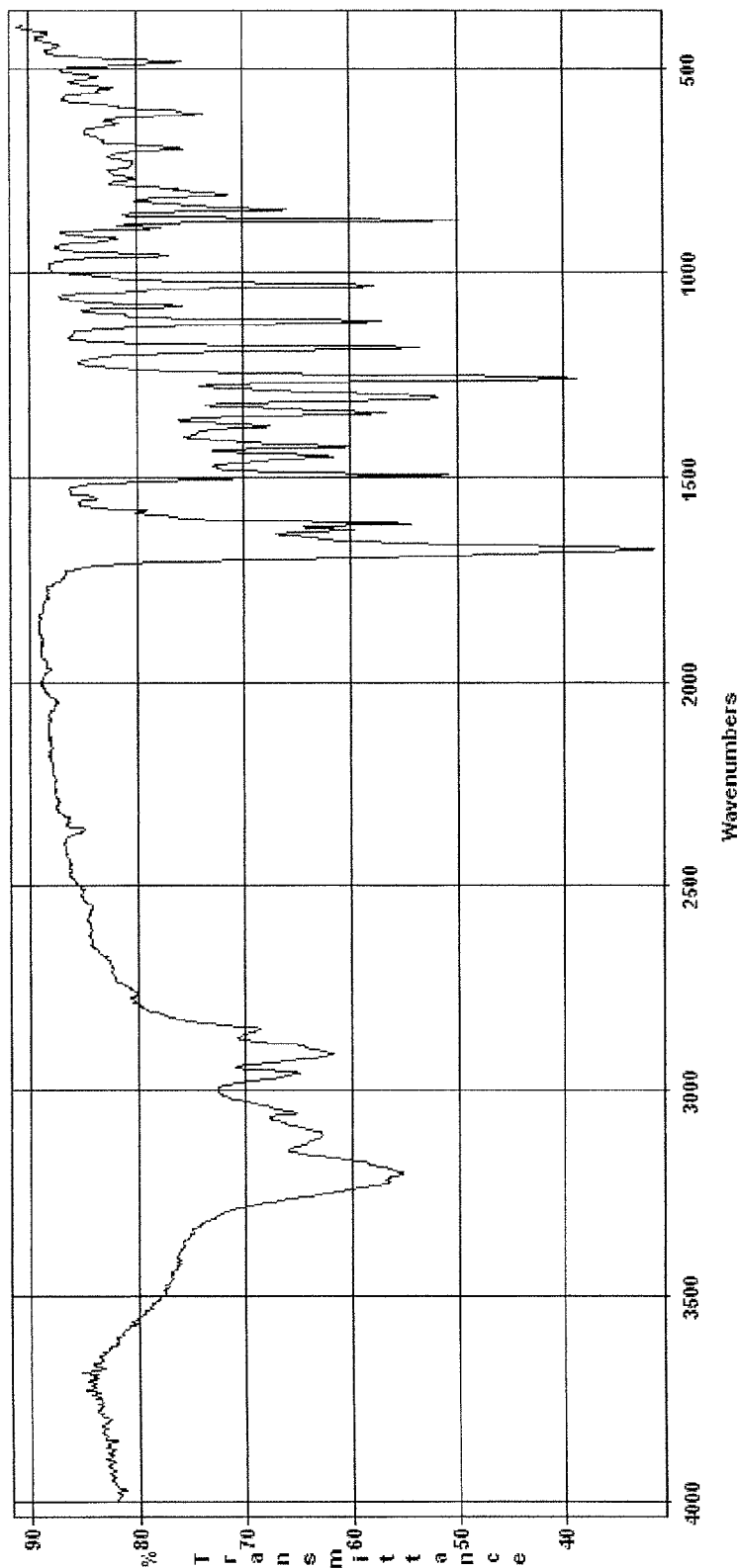

The results of the detection and analysis were represented in FIG. 4.

The most characteristic peaks of powder X-ray diffraction analysis were: peaks at Bragg angles (2θ) of 7.88°, 14.45° and 17.94° (with relative intensities of 100%, 58% and 49%, respectively).

The most characteristic peaks of DSC analysis were: desolvatation and melting at 147-153° C. with a minimum at 150° C., followed by recrystallisation at 185-217° C. with a maximum at 200° C., and two endothermic peaks at 223° C. and 237° C.

The most characteristic peaks of IR spectroscopy analysis were, expressed in cm-1: 3055, 2840 (more intense than with form D), 1628, 872, 845, 808.

Example 3

Preparation of Pimobendan Crystalline Form A
(Pimobendan Polymorph A)

Pimobendan dioxane solvate (200.0 g, assay 79.3%, 0.4743 mol), prepared as described in Example 2, was stirred with toluene (2000±200) ml). The reaction mixture was heated to boiling temperature (107-108° C.), maintained at this temperature for 3.5 (3-4) hours, and the hot mixture was filtered on a suction funnel. After that, the precipitate was rinsed with toluene (400±50 ml), filtered and dried at (115-120) ° C. at reduced pressure for about (15-20) hours until the residual solvent concentration was: toluene<890 ppm, 1,4-dioxane<380 ppm.

Pimobendan crystalline form A (pimobendan polymorph A) complies with the European Pharmacopoeia (Ph. Eur.) reference standard) was obtained as a white powder (156.0 g, assay 100.9%, related substances<0.05%, melting temperature 241° C., content of water 0.22%). The yield of this process was 98.1% (average (99.0±1.0) %). The melting temperature was 241-244° C.

Figure 2A:
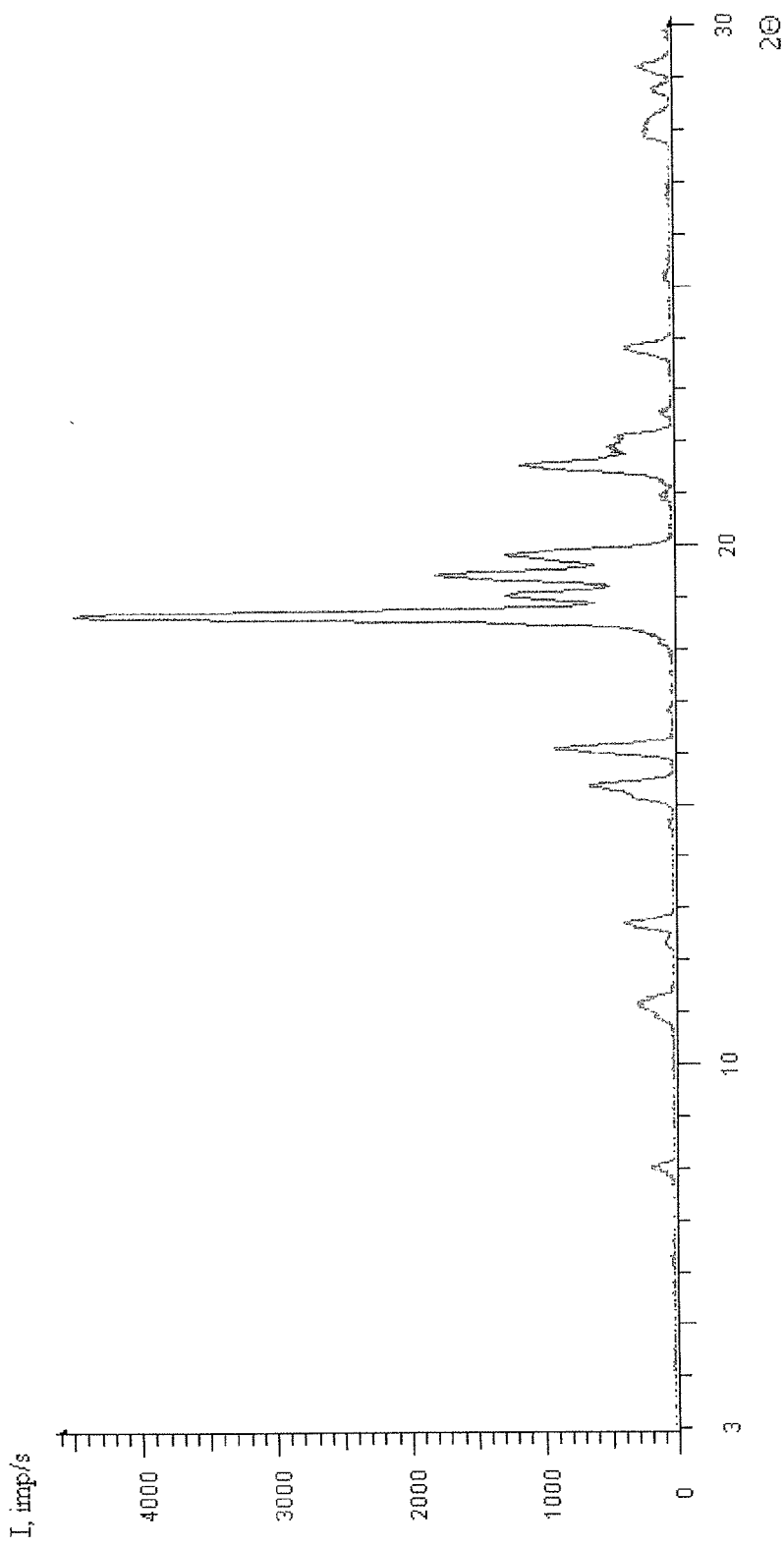
FIG. 2 represents the results of powder X-ray diffraction analysis (FIG. 2A), differential scanning calorimetry (DSC) (FIG. 2B) and infrared (IR) spectroscopy (FIG. 2C) of crystalline form A of pimobendan. The methods for detection and analysis were as described in the section "Materials and methods used for analysing crystalline forms of pimobendan".
Figure 2B:
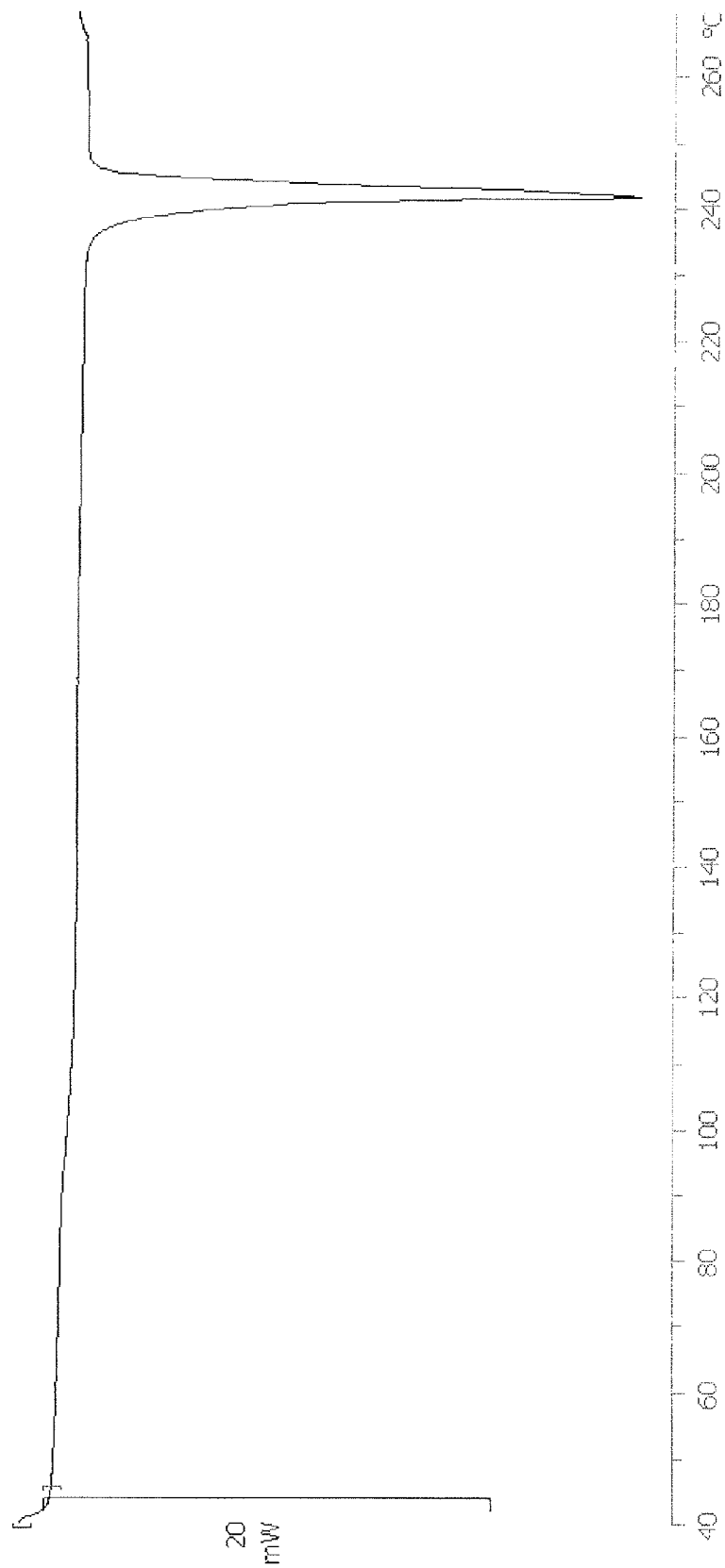
Figure 2C:
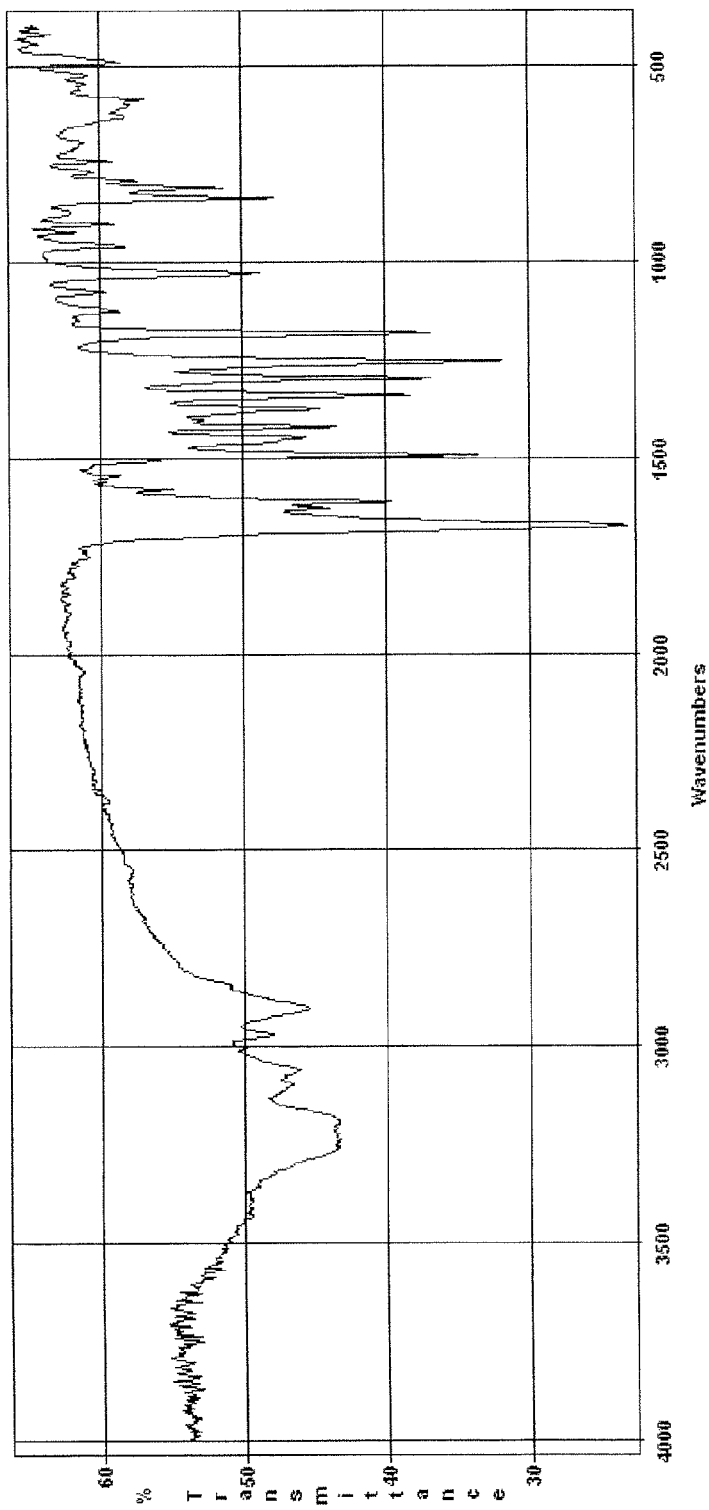

The results of the detection and analysis were represented in FIG. 2.

The most characteristic peak of X-ray diffraction analysis was: peaks at Bragg angles (2θ) of 12.69°, 18.67° and 19.42° (with relative intensities of 9%, 100% and 37%, respectively).

The most characteristic peak of DSC analysis was: one endothermic peak corresponding to melting at 241-244° C.

The most characteristic peaks of IR spectroscopy analysis were, expressed in cm-1: 3200 (broad), 2900 (vC—H alif.; more intense than for form B); 1671 (vC=O), 837 (δC—H arom.), 810 (δC—H arom.).

Example 4

Preparation of Pimobendan Crystalline Form D
(Pimobendan Methanol Solvate)

Pimobendan crystalline form A (pimobendan polymorph A) (5.0 g), prepared as described in Example 3, was ground with methanol (4-5 ml) in a mortar and pestle under a dry atmosphere, until the methanol evaporated. Pimobendan crystalline form D was obtained as a dry, white powder (5.4 g, assay 92.0%, related substances<0.05%, content of water 0.79%, loss on drying 8.2%, content of methanol 6.6%). The yield of this process was 98.0%.

Figure 5A:
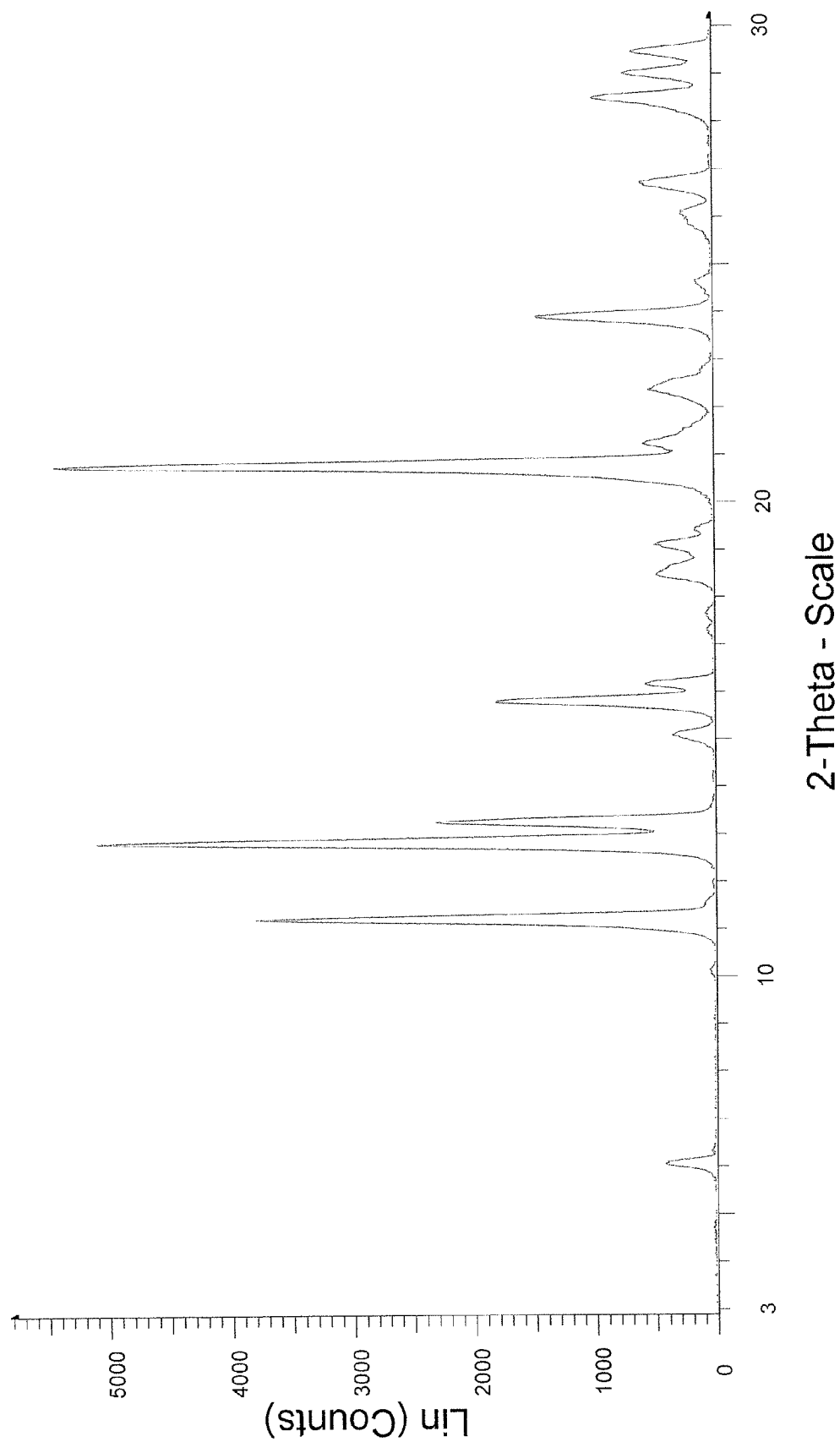
FIG. 5 represents the results of powder X-ray diffraction analysis (FIG. 5A), differential scanning calorimetry (DSC) (FIG. 5B) and infrared (IR) spectroscopy (FIG. 5C) of crystalline form D of pimobendan. The methods for detection and analysis were as described in the section "Materials and methods used for analyzing crystalline forms of pimobendan".
Figure 5B:
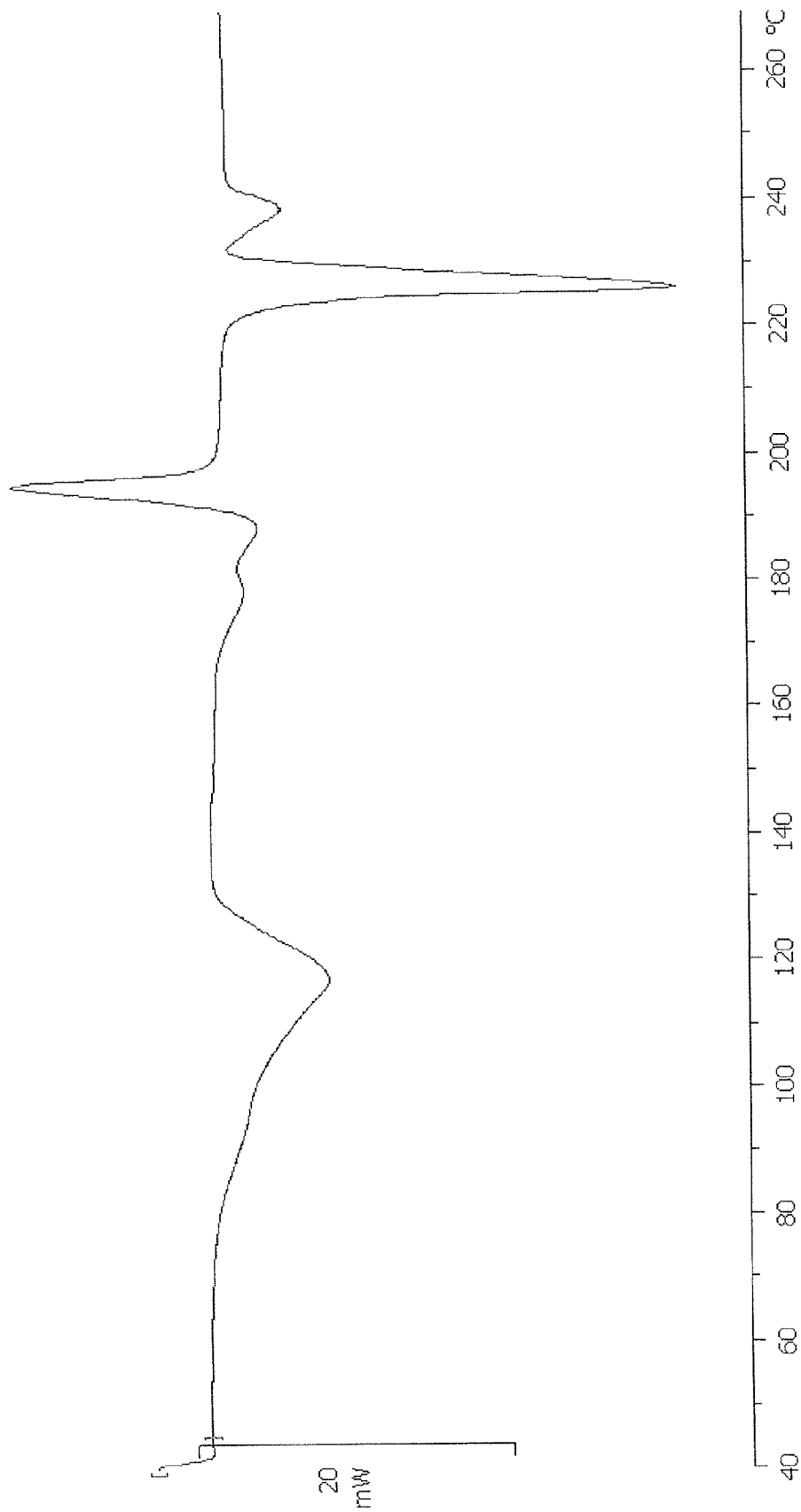
Figure 5C:
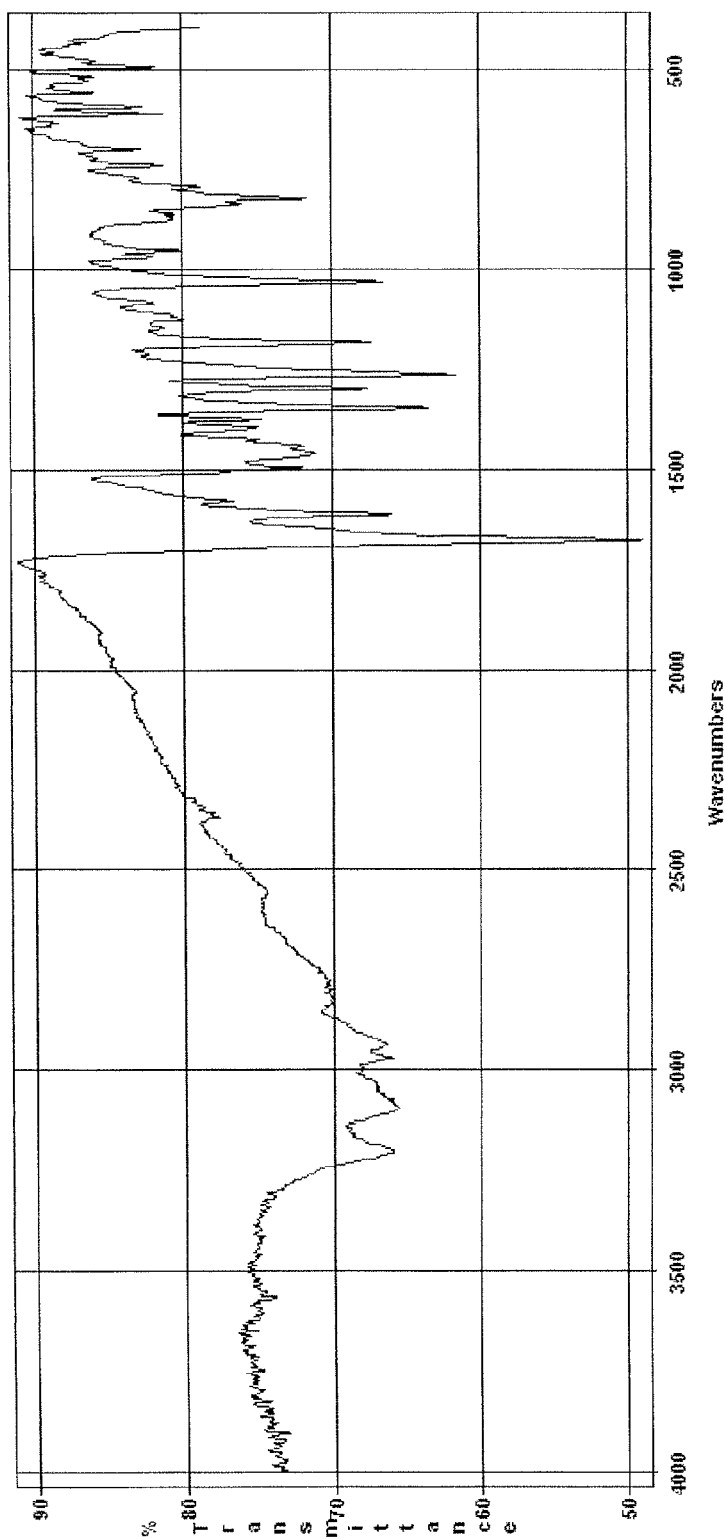

The results of the detection and analysis were represented in FIG. 5.

The most characteristic peaks of powder X-ray diffraction analysis were: peaks at Bragg angles (2θ) of 11.20°, 12.82° and 20.80° (with relative intensities of 70%, 94% and 100%, respectively).

The most characteristic peaks of DSC analysis were: desolvatation at 97-129° C. with a minimum at 117° C., melting at 137-162° C. with a minimum at 152° C., followed by recrystallisation and two endothermic peaks at 226° C. and 238° C.

The most characteristic peaks of IR spectroscopy analysis were, expressed in cm-1: 3554, 2840 (very weak), 839, 823.

Example 5

Preparation of Pimobendan Crystalline Form B
(Pimobendan Polymorph B)

Pimobendan crystalline form D (pimobendan methanol solvate) (5.0 g), prepared as described in Example 4, was heated at 65 (60-70)° C. for 3.5 (3-4) hours in a ~0.5 cm thick layer.

Pimobendan crystalline form D (pimobendan polymorph B was obtained as a white powder (4.5 g, assay 100.0%, related substances<0.05%, content of water 0.21%, content of methanol<30 ppm). The yield was 99.0%. The melting temperature was 188° C.

Figure 3A:
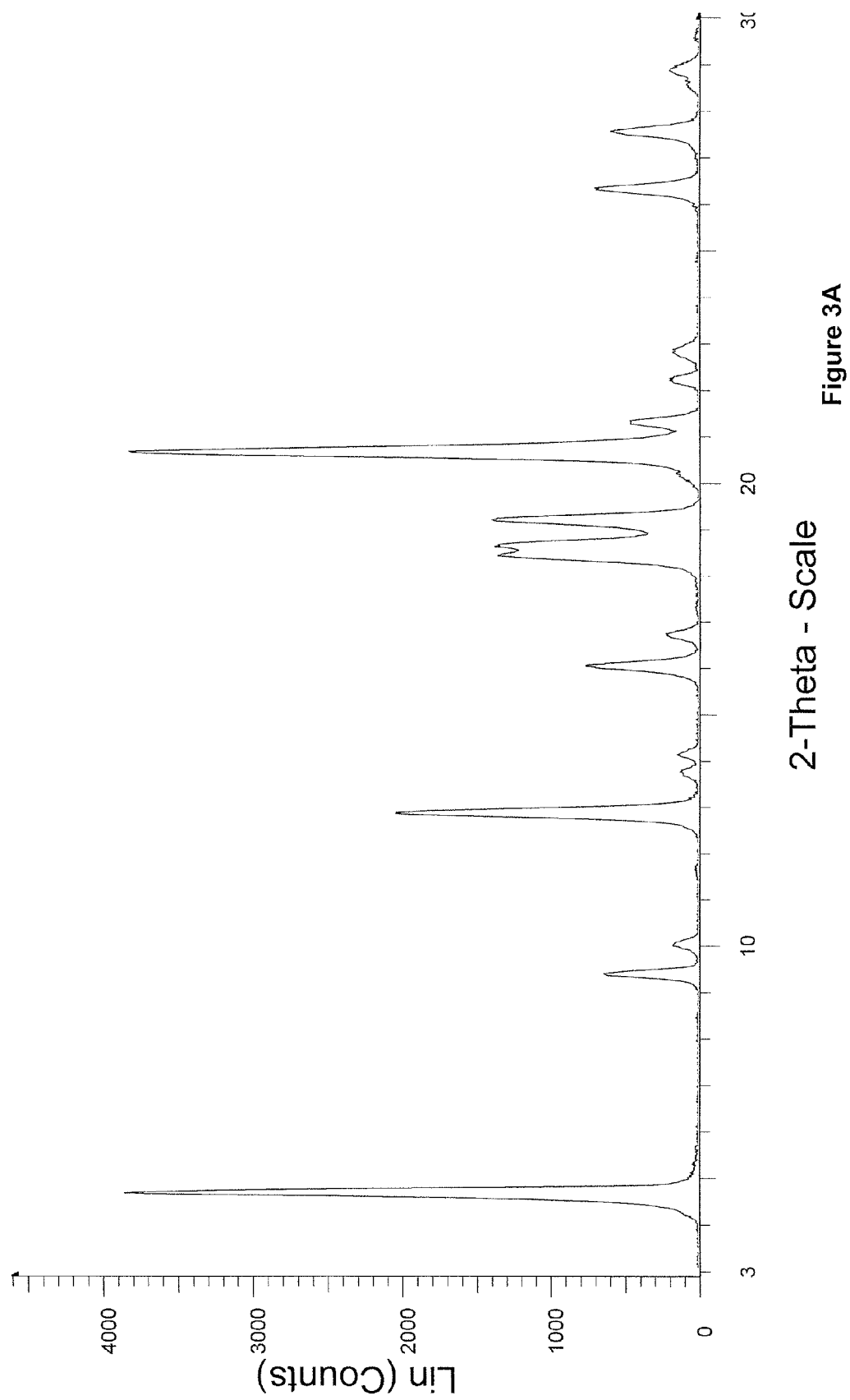
FIG. 3 represents the results of powder X-ray diffraction analysis (FIG. 3A), differential scanning calorimetry (DSC) (FIG. 3B) and infrared (IR) spectroscopy (FIG. 3C) of crystalline form B of pimobendan. The methods for detection and analysis were as described in the section "Materials and methods used for analyzing crystalline forms of pimobendan".
Figure 3B:
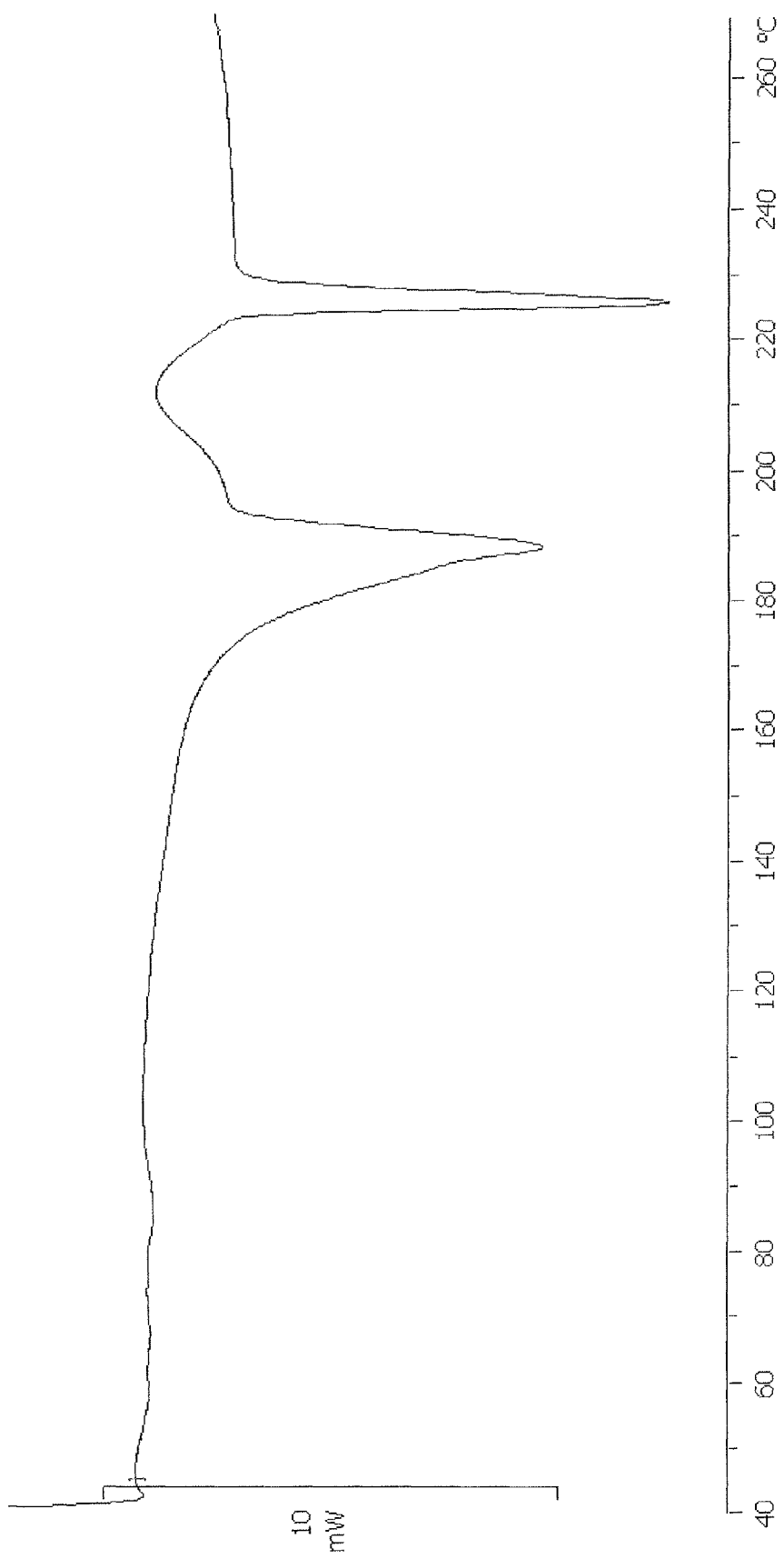
Figure 3C:
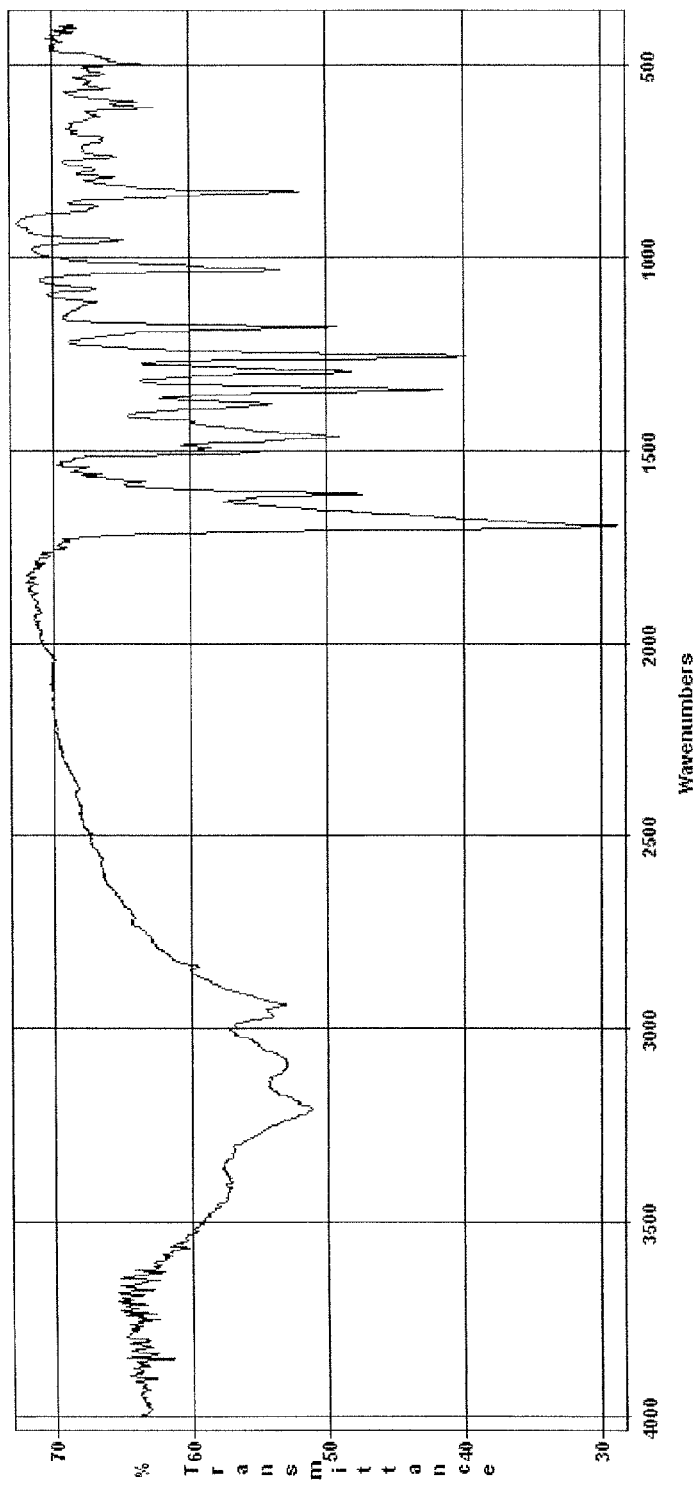

The results of the detection and analysis were represented in FIG. 3.

The most characteristic peaks of powder X-ray diffraction analysis were: peaks at Bragg angles (2θ) of 4.65°, 12.90° and 20.70° (with relative intensities of 100%, 53% and 99%, respectively).

The most characteristic peaks of DSC analysis were: one first, broad, endothermic peak at 181-193° C. with a minimum at 188° C., an exothermic peak at 200-223° C. with a maximum at 212° C., and a second endothermic peak at 226° C.

The most characteristic peaks of IR spectroscopy analysis were, expressed in cm-1: 3400 (small peaks), 2900 (vC—H alif; smaller than with form A); 1793 (vC:O).

Example 6

Results of the Analysis of the Crystalline Forms of Pimobendan

DSC analysis.

Pimobendan polymorph A has one endothermic peak corresponding to its melting at 241° C.

The DSC curve of polymorph B shows two endothermic peaks: the first is a broad peak at 181-193° C. with a minimum at 188° C., followed by an exothermic peak at 200-223° C. with a maximum at 212° C., and the second endothermic peak at 226° C. The first endothermic peak is attributed to the melting of form B immediately followed by recrystallization of B to the high melting polymorph D. The second peak is due to melting of form D.

The DSC curve of the dioxane solvate shows desolvatation and melting process at the temperature range 147-153° C.

with minimum at 150° C., followed by recrystallization to the high melting polymorphs D and A at 185-217° C. with maximum at 200° C. Two endothermic peaks follow at 223° C. and 237° C. The first peak is due to melting of form D, the second is due to melting of form A.

The DSC curve of methanol solvate shows desolvatation at the temperature range 97-129° C. with a minimum at 117° C. From 137° C. to 162° C. with a minimum at 152° C. the form B melts, immediately followed by recrystallization to the high melting polymorphs D and A. Two endothermic peaks follow at 226° C. and 238° C. The first peak is due to melting of form D, the second is due to melting of form A.

IR spectra.

Pimobendan: 3230, 3180 (vN—H), 3060 (vC—H arom.), 2970, 2900 (vC—H alif.), 1670 (vC=O), 1610 (vC=N), 1490, 1440 (vC=C), 1420, 1370, 1250 (δC—H alif.), 1180 (vC—O), 1030 (vC—O alif.), 840, 810 (δC—H arom) cm-1.

The most noticeable differences between form A and form B are at approximately 3400 cm-1, where there are some small peaks for form B, but no for form A. Also there is differences for amide N—H stretching at 3200 cm-1 where there is broader peak for form A and at 2900 cm-1 where there has bigger peak for form A comparing with form B. There is the characteristic carbonyl stretching at 1671 cm-1 for form A, but for form B this peak is shifted to 1693 cm-1. Differences are observed also in region 1400-1480 cm-1, which is due to different C—H bending in methyl groups. In region between 800 and 850 cm-1 there are two peaks for A at 837 cm-1 and 810 cm-1.

There are absorption peaks at 3554 cm-1 for form D due to hydrogen bonding from methanol molecules in the structure, while there is no absorption at that wavelength for form C. There are small differences in wavenumbers from 3070 to 3250 cm-1, but there is an absorption at 3055 cm-1 for form C. In the region between 2830 and 2980 cm-1 there are three peaks at approximately the same position for form D and form C. The peaks at approximately 2840 cm-1 are more intensive for form C, but almost invisible for methanol solvate. In double bond stretching region the only difference is peak at 1628 cm-1 for form C which is absent for other solvates. There are small changes of position but notable intensity changes of peaks in the region between 1000 and 1500 cm-1. In the 800 to 880 cm-1 region there is one double peak for form D (839 cm-1 and 823 cm-1), but three peaks for form C (872 cm-1, 845 cm-1 and 808 cm-1).

1H-NMR spectra.

Pimobendan Analysis by Solution Phase 1H-NMR.

Pimobendan $^1$H-NMR shows two sets of signals due to the restricted rotation around the bond linking two six-member rings. The asymmetric methyl group interacts differently with the rest of the protons in each of these rotamers.

i. 1H-NMR (DMSO-d6, δ, m.d.):

| | |
|---|---|
| 1.12 (d) | CH3 total 3H |
| 1.13 (d) | |
| 2.25 (d) | CH2 total 2H |
| 2.26 (d) | |
| 2.71 (dd) | |
| 2.72 (dd) | |
| 3.47 (dq) | CH total 1H |
| 3.52 (dq) | |
| 3.84 (s) | OCH3 total 3H |
| 7.12 (d) | CH anisole total 2H |
| 8.11 (d) | |
| 7.51 (d) | CH benzimidazole total 3H |
| 7.63 (d) | |
| 7.67 (dd) | |

-continued

| | |
|---|---|
| 7.73 (dd) | |
| 7.84 (d) | |
| 8.00 (d) | |
| 10.88 (s) | NH total 1H |
| 10.91 (s) | |
| 12.84 (s) | NH benzimidazole total 1H |
| 12.87 (s) | |

Pimobendan Methanol Solvate 1.12 (3H, d, J=6.8 Hz, CH3), 2.26 (1H, d, J=16.6 Hz, CH2-ax), 2.72 (1H, dd, J=16.6 and 6.8 Hz, CH2-eq), 3.50 (1H, m, J=6.8 Hz, CH), 3.84 (3H, s, OCH3), 7.12 (2H, d, J=8.6 Hz, Harom.), 7.50-8.00 (3H, broad m, Hbenzmidazole), 8.12 (2H, d, J=8.6 Hz, Harom.), 10.90 (1H, s, NH), 12.86 (1H, bs, NHbenzimidazole).

Pimobendan Dioxane Solvate.

1H-NMR (DMSO-d6, δ, m.d.): 1.13 (3H, d, J=7.2 Hz, CH3), 2.26 (1H, d, J=16.7 Hz, CH2-ax), 2.72 (1H, dd, J=16.5 and 6.7 Hz, CH2-eq), 3.50 (1H, m, CH), 3.55 (8H, s, dioxan), 3.84 (3H, s, OCH3), 7.12 (2H, d, J=8.8 Hz, Harom.), 7.52-8.00 (3H, m, Hbenzmidazole), 8.12 (2H, d, J=8.8 Hz, Harom.), 10.88 (1H, s, NH), 12.86 (1H, bs, NHbenzimidazole).

The 1H-NMR data confirm the chemical identity of all samples, including the protonation state (indicating that these crystal forms are not salts). The elemental composition agrees well with the stated chemical identity of all presented crystal forms.

The invention claimed is:

1. A pharmaceutical composition containing crystalline pimobendan, the structural formula of which is:

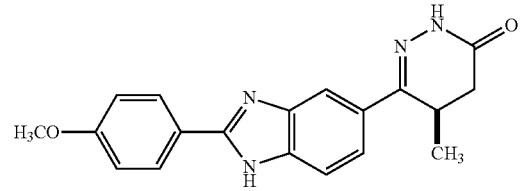 [SMILES: COc1ccc(-c2nc3cc(C4=NNC(=O)C[C@H]4C)ccc3[nH]2)cc1]

wherein the pharmaceutical composition includes no organic acid that is therapeutically inactive, and wherein the crystalline pimobendan is selected from the group consisting of:
(i) form A, the diffraction pattern using powder X-ray diffractometry of which has peaks at Bragg angles (2θ) of 12,69°, 18,67° and 19,42°, with relative intensities of 9%, 100% and 37%, respectively, as the most characteristic peaks;
(ii) form B, the diffraction pattern using powder X-ray diffractometry of which has peaks at Bragg angles (2θ) of 4,65°, 12,90° and 20,70°, with relative intensities of 100%, 53% and 99%, respectively, as the most characteristic peaks:
(iii) form C, a dioxane solvate, of which the diffraction pattern using powder X-ray diffractometry of which has peaks at Bragg angles (2θ) of 7,88°, 14,45° and 17,94°, with relative intensities of 100%, 58% and 49%, respectively, as the characteristic peaks;
(iv) form D, a methanol solvate, of which the diffraction pattern using powder X-ray diffractometry of which has peaks at Bragg angles (2θ) of 11,20°, 12,82° and 20,80°, with relative intensities of 70%, 94% and 100%, respectively, as the most characteristic peaks.

2. The pharmaceutical composition of claim 1, selected from the group consisting of:
   (i) form A, further having the following characteristic peak using differential scanning calorimetry: one endothermic peak corresponding to melting at 241-244° C.;
   (ii) form B, further having the following characteristic peaks using differential scanning calorimetry: one first, broad, endothermic peak at 181-193° C. with a minimum at 188° C., an exothermic peak at 200-223° C. with a maximum at 212° C., and a second endothermic peak at 226° C.,
   (iii) form C, further having the following characteristic peaks using differential scanning calorimetry: desolvatation and melting at 147-153° C. with a minimum at 150° C., and recrystallisation at 185-217° C. with a maximum at 200° C., and two endothermic peaks at 223° C. and 237° C., and
   (iv) form D, further having the following characteristic peaks using differential scanning calorimetry: desolvatation at 97-129° C. with a minimum at 117° C., melting at 137-162° C. with a minimum at 152° C., and recrystallisation and two endothermic peaks at 226° C. and 238° C.

3. The pharmaceutical composition of claim 1, selected from the group consisting of:
   (i) form A, further having the following characteristic peaks of the IR spectrum obtained by using infrared (IR) spectrometry, expressed in cm$^{-1}$: 3200(broad), 2900 ($\nu_{C-H}$ alif.; more intense than for form B); 1671 ($\nu_{C=O}$), 837 ($\delta_{C-H}$arom.). 810 ($\delta_{C-H}$arom.),
   (ii) form B, further having the following characteristic peaks of the IR spectrum obtained by using infrared (IR) spectrometry, expressed in cm$^{-1}$: 3400 (small peaks), 2900 ($\nu_{C-H}$alif.; smaller than with form A); 1793 ($\nu_{C:O}$),
   (iii) form C, further having the following characteristic peaks of the IR spectrum obtained by using infrared (IR) spectrometry, expressed in cm$^{-1}$: 3055, 2840(more intense than with form D), 1628, 872, 845, 808, and
   (iv) form D, further having the following characteristic peaks of the IR spectrum obtained by using infrared (IR) spectrometry, expressed in cm$^{-1}$: 3554, 2840(very weak), 839, 823.

4. The pharmaceutical composition of claim 1 and at least one other therapeutically active ingredient.

5. The pharmaceutical composition of claim 4, wherein the other therapeutically active ingredient is selected from the group consisting of: a calcium channel blocker, aldosteron antagonist, loop diuretic, thiazide diuretic, prostaglandin, ACE inhibitor, digitalis glycoside, β-blocker, angiotensin II receptor antagonist, and phosphodiesterase type 5 inhibitor.

6. The pharmaceutical composition of claim 1, together with carriers and excipients.

7. A pharmaceutical composition according to claim 6, containing at least one other therapeutically active ingredient.

8. A pharmaceutical composition according to claim 7, wherein the other therapeutically active ingredient is selected from the group consisting of: a calcium channel blocker, aldosteron antagonist, loop diuretic, thiazide diuretic, prostaglandin, ACE inhibitor, digitalis glycoside, β-blocker, angiotensin II receptor antagonist, and phosphodiesterase type 5 inhibitor.

9. A pharmaceutical composition according to claim 6, wherein the composition is formulated in a form suited for oral administration.

10. A pharmaceutical composition according to claim 6, in combination with packaging material suitable for the pharmaceutical formulation, said packaging material including instructions for therapeutically using of the pharmaceutical formulation.

* * * * *